United States Patent [19]

Brooker et al.

[11] 4,376,125

[45] Mar. 8, 1983

[54] AMINOBENZLPROPRANOLOL AND PHARMACEUTICAL PREPARATION THEREOF

[75] Inventors: Gary Brooker, Charlottesville, Va.; Wesley L. Terasaki, Miami, Fla.; Joel M. Linden, Charlottesville, Va.

[73] Assignee: University of Virginia Alumni Patents Foundation, Charlottesville, Va.

[21] Appl. No.: 204,199

[22] Filed: Nov. 5, 1980

[51] Int. Cl.$^3$ ..................... C07C 87/28; A61K 31/135
[52] U.S. Cl. ..................... 424/330; 424/316; 260/501.17; 564/350; 564/349; 564/381
[58] Field of Search ............. 564/381, 349, 350; 424/330, 316; 260/501.17

[56] References Cited

U.S. PATENT DOCUMENTS

| | | | |
|---|---|---|---|
| 2,590,079 | 3/1952 | Abell et al. | 564/381 |
| 3,337,628 | 8/1967 | Crowther et al. | 564/349 |
| 4,161,542 | 7/1979 | Carlsson et al. | 424/330 |

FOREIGN PATENT DOCUMENTS

| | | | |
|---|---|---|---|
| 401167 | 7/1967 | Austria | 564/349 |
| 1066613 | 4/1967 | United Kingdom | 564/349 |

OTHER PUBLICATIONS

Terasaki et al., Proc. Natl. Acad. Sci. USA, vol. 76, No. 12, pp. 6401–6405, Dec. 1979.
Crowther et al., Jour. Med. Chem., vol. 11 (1968), pp. 1009–1013.

*Primary Examiner*—Bernard Helfin
*Attorney, Agent, or Firm*—Oblon, Fisher, Spivak, McClelland & Maier

[57] ABSTRACT

1-(p-Amino-α,α-dimethylphenethylamino)-3-(1-naphthoxy)-2-propanol, 1-(p-hydroxy-α,α-dimethylphenethylamino)-3-(1-naphthoxy)-2-propanol, 1-(p-methyl-α,α-dimethylphenethylamino)-3-(1-naphthoxy)-2-propanol, 1-(p-methoxy-α,α-dimethylphenethylamino)-3-(1-naphthoxy)-2-propanol and the pharmaceutically acceptable acid addition salts thereof are effective, long lasting β-adrenergic blocking agents and areas of indication are hypertension, angina pectoris, cardiac arrythmia, and the like.

3 Claims, 5 Drawing Figures

AMINOBENZLPROPRANOLOL AND PHARMACEUTICAL PREPARATION THEREOF

BACKGROUND OF THE INVENTION

1. Field of the Invention

The present invention relates to a compound which exhibits β-adrenergic blocking activity. More particularly, the present invention relates to a pharmaceutically active compound related to the known β-receptor blocking agent, propranolol.

2. Description of the Prior Art

Numerous compounds are known which exhibit β-receptor blocking activity and therefore are useful in the treatment of heart and vascular dieseases such as angina pectoris, hypertension, vasoregulatoric neurasteni and some forms of arrythmia. For example, U.S. Pat. Nos. 4,036,988 and 4,039,685 show 1-phenoxy-2-hydroxy-3,5-butylamino propane derivatives which exhibit bradycardia and block isoproterenol activity. U.S. Pat. No. 3,998,790 shows a series of para-substituted phenoxy-hydroxy-propylamines which are therapeutically effective by their ability to block the β-receptors of heart tissue. U.S. Pat. Nos. 3,337,628 and 3,432,545 show a number of propanolamine compounds which exhibit a β-adrenergic blocking activity of which some derivatives contain a 1-naphthoxy substituent and the primary amino group is substituted by one or two alkyl or aralkyl radicals. An important conventional compound which contains a 1-naphthoxy substituent is propranolol which is a strong β-adrenergic blocking agent. However, a disadvantage of propranolol is that it does not exhibit the degree of longevity of binding to β-adrenergic receptors in mammalian cells that is desirable for β-adrenergic blocking agents. Another disadvantage of propranolol is that patients who are taken off of propranolol suddenly or who abruptly stop taking the drug against medical advice may precipitate severe angina or myocardial infarction. Moreover, propranolol must be administered several times a day which is a factor in poor patient compliance in taking the drug. Still further, because of the frequency which propranolol must be taken, there is a concomitant increased risk of medication error.

SUMMARY OF THE INVENTION

Accordingly, one object of the present invention is to provide a β-adrenergic blocking agent which bonds to β-adrenergic receptors in cells with increased tenacity and for unusually long periods of duration.

Briefly, this object and other objects of the present invention as hereinafter will become more readily apparent can be achieved by a compound which exhibits β-adrenergic receptor blocking activity of the formula:

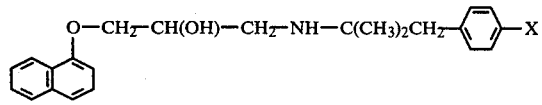

wherein X is amino, hydroxy, methyl or methoxy, or a pharmaceutically acceptable acid addition salt thereof.

BRIEF DESCRIPTION OF THE DRAWINGS

A more complete appreciation of the invention and many of the attendant advantages thereof will be readily obtained as the same becomes better understood by reference to the following detailed description when considered in connection with the accompanying drawings, wherein.

DESCRIPTION OF THE PREFERRED EMBODIMENTS

Figure 1A:
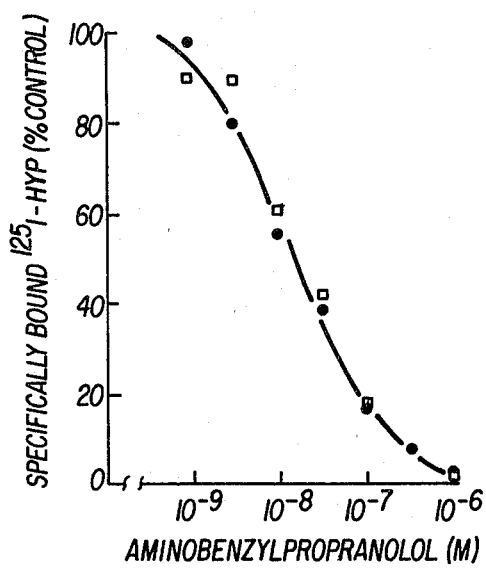
FIG. 1 shows two graphs which demonstrate the inhibition of specific ($^{125}$I)-iodohydroxybenzylpindolol binding by aminobenzylpropranolol and propranolol.

The β-adrenergic blocking agent of the present invention constitutes a group of four compounds which are aminobenzylpropranolol [1-(p-amino-α,α-dimethylphenethylamino)-3-(1-naphthoxy)-2-propanol], hydroxybenzylpropranolol [1-(p-hydroxy-α,α-dimethylphenethylamino)-3-(1-naphthoxy)-2-propanol], methylbenzylpropranolol [1-(p-methyl-α, α-dimethylphenethylamino)-3-(1-naphthoxy)-2-propanol], and methoxybenzylpropranolol [1-(p-methoxy-α,αdimethylphenethylamino)-3-(1-naphthoxy)-2-propanol]. The pharmaceutically acceptable salts of the present β-adrenergic receptor blocking compound are also within the scope of the present invention such as the acetate, chloride, and phosphate salts. The outstanding property of the present compound is its unexpected ability to tenaciously bind to β-adrenergic sites in a host subject for prolonged periods of time thus exhibiting a quasi-irreversible bonding effect on β-adrenergic receptors. It is believed that the outstanding characteristic of the present compounds is attributable to the hydrophobicity of the molecule.

The β-adrenergic receptor blocking compound of the invention can be prepared by any convenient technique generally involving known reaction methodology, for instance, as shown in U.S. Pat. Nos. 4,039,685 and 3,935,267. A preferred method of synthesis involves the reaction between p-substituted-α,α-dimethylphenethylamine or derivatives thereof with α-naphthoxy-1-propane-2, 3-oxide or derivatives thereof. The propane oxide reactant can be readily prepared by reacting an epihalohydrin compound with γ-naphthol or derivative thereof. All of the above individual reactions constitute known reaction methodology and can be conducted under standard reaction conditions. The reactants can be reacted in roughly equimolar amounts at a reaction temperature generally ranging from 0° to 100° C.

The β-adrenergic receptor blocking compound of the present invention and its non-toxic pharmacological acceptable acid addition salts have a variety of useful purposes. The present compound and its salts produce bradycardia and simultaneously act as N-isopropylnoradrenaline (isoproterenol) antagonists. Thus, the tachycardiac effects caused by the administration of isoproterenol are suppressed or eliminated by prior administration of the present compound or salt thereof, and cardiac arrhythmia is equalized by the compound and its salts. Accordingly, the indicated areas of use of the present compound are in the treatment of hypertension, angina pectoris, cardiac arrhythmia, digitalis intoxication and pheochromocytoma disorders. The present compound and its salts may also be used in conjunction with coronary dilator or sympatheticomimetic agents.

For the administration of the present β-adrenergic receptor blocking compound, a pharmaceutically effective quantity of the compound or at least one of its salts is combined with a major portion of a pharmaceutically acceptable carrier. The composition may be in the form of injectable solutions or suspensions, tablets, dragees, sustained release tablets and the like. Normally, the dose of compound administered orally ranges from 1 to 300 mg, preferably 1 to 150 mg, while for parental administration the dosage ranges from 1 to 20 mg.

In order to induce antiarrhythmic activity in warm-blooded animals, the animals are administered a safe and antiarryhythmically effective amount of the present compound or a salt thereof. The compound can be administered orally, parentally or rectally in dosage units of mg/kg of body weight depending on the method of administration.

The compound of the present invention is also useful as an investigational tool in several ways. Because it effectively acts as a β-adrenergic blocking agent over long periods, it is an effective agent for reducing or virtually eliminating β-adrenergic receptors from cell surface membranes. By being labeled with an appropriate radioactive specie, the present compound in radiolabeled form can be utilized as a β-adrenergic receptor ligand. Radiolabeling can be accomplished with radioactive iodine by standard techniques. Alternatively, the blocking agent can be synthesized in tritium labeled form.

In the case of aminobenzylpropranolol, it can be diazotized and converted to an azido group by standard reaction methodology, thereby rendering aminobenzylpropranolol useful as a true photoaffinity label. In the event it is desireable to immobilize aminobenzylpropranol on a solid support such as agarose or the like, on a high molecular weight polymer such as dextran, phenylalanine, or the like or on an electron-dense or fluorescently tagged protein such as ferritin or the like, the terminal aromatic amine substituent can be modified such as by carbodiimide coupling or reaction with N-hydroxysuccinimide derivatives by standard reaction methodology. Aminobenzylpropranolol immobilized in this manner is useful in isolating the β-adrenergic receptor.

The ability of the present β-adrenergic receptor blocking compound to function as an effective β-adrenergic blocking agent for the selective elimination of cellular β-adrenergic receptors is apparent from the following study on the interaction of aminobenzylpropranolol with glioma cells and mammalian atrium cells. For the study involving glioma cells, C6 rat glioma cells, 2B subclone were grown in monolayer cultures by the technique described by Terasaki et al, J. Biol. Chem., 253, 5418–5425 in 16 mm plastic cluster dishes. In all experiments, the cells were changed from Ham's F-10 containing 10% fetal bovine serum growth medium to a simple salt medium containing 130 mM NaCl, 4 mM KCl, 0.6 mM $MgSO_4$, 0.3 mM $CaCl_2$, 5 mM sodium phosphate buffer (pH 7.4). All washing experiments involving glioma cells utilized this salt solution as the wash medium. In experiments involving the glioma cells, specific (propranolol-displaceable) binding of ($^{125}I$)-iodohydroxybenzylpindolol to C6 rat glioma cells was performed by the method developed by Terasaki et al (see above reference) with the exception that in all solutions phentolamine was omitted, and at the termination of the radioligand binding reaction, 0.1 mM (±)-propranolol was included in the cell wash solution.

The results of the experiments involving cultured glioma cells show that aminobenzylpropranolol is a relatively potent β-adrenergic antagonist, displacing the specific radioligand, ($^{125}I$)-iodohydroxybenzylpindolol, from β-adrenergic receptors in intact living cells. This fact is demonstrated in FIG. 1 wherein FIG. 1A is a displacement curve obtained by treating glioma cells for 40 min. at 37° C. with aminobenzylpropranolol and then specific [$^{125}I$]-iodohydroxybenzylpindolol binding (●) was mesured as described by the above referenced Terasaki et al publication. In other test plates, the cells were pretreated with aminobenzylpropranolol blocking agent and then washed repeatedly over a period of 3 hours at 37° C. before determination of [$^{125}I$]-iodohydroxybenzylpindolol binding (□). For all points, n=3, which means that each data point is an average of three separate determinations. There was no significant difference between the ability of aminobenzylpropranolol to block β-adrenergic receptors assayed acutely. FIG. 1a shows an apparent $K_D$ of 8 nM for aminobenzylpropranolol in blocking one-half of the β-receptors in 40 minutes. (This value was corrected for competition by ($^{125}I$)-iodohydroxybenzylpindolol).

Figure 1B:
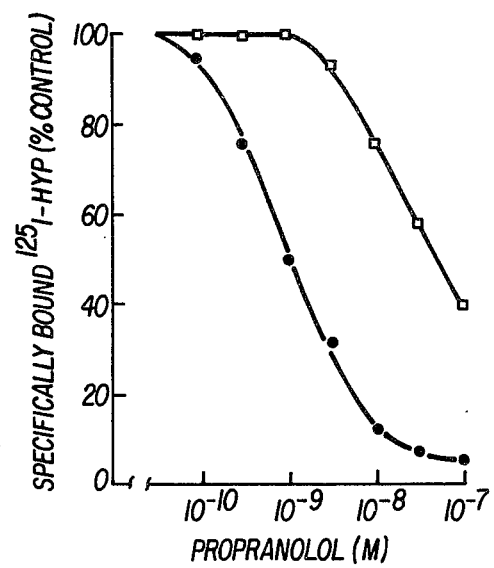

FIG. 1b, in contrast, shows the displacement curves obtained when the conventional β-adrenergic blocking agent, (−)-propranolol, was employed in a comparative test. In the test glioma cells were treated for 40 minutes at 37° C. with (−) propranolol and then specific ($^{125}I$)-iodohydroxybenzylpindolol binding (●) was measured by the method referenced above. For all points, n=3, (The washing experiments of cultured C6 cells could not be conducted beyond 5–6 hours because specific ($^{125}I$)-iodohydroxybenzylpindolol binding diminished markedly after this time period as evidenced by the curve denoted by the symbol (□)). The apparent $K_d$ for propranolol (1 mM) was increased 50 fold after washing with salt solution, suggesting a 98% wash-out of (−)-propranolol.

Figure 2:
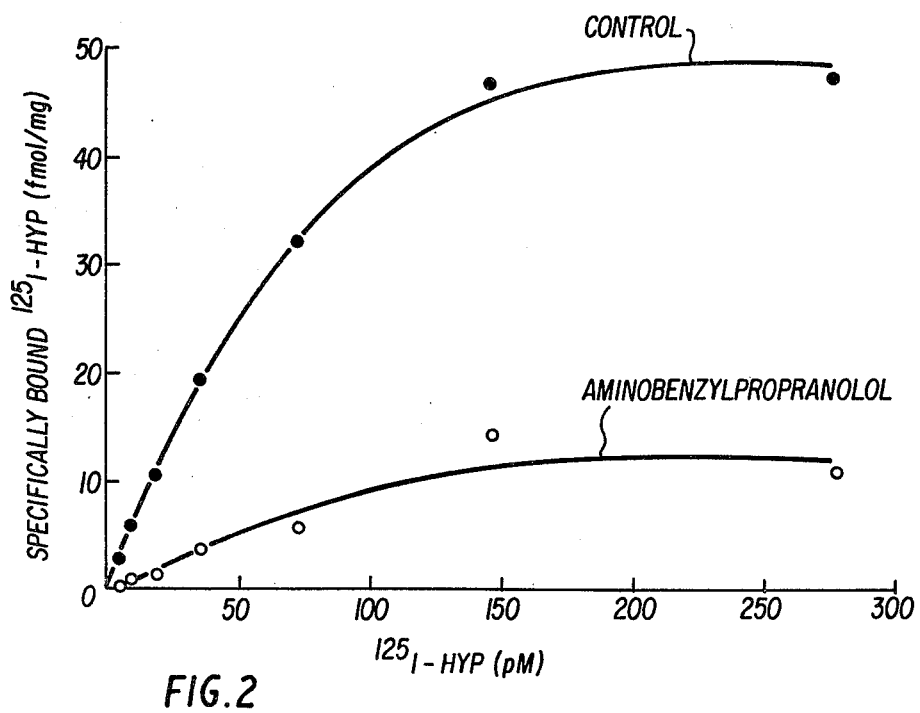
FIG. 2 shows that glioma cells treated with aminobenzylpropranolol and then washed with salt solution display a marked reduction in maximum receptor binding.

It would be predicted that the occupation of a receptor by a specific ligand should be considered as an effective loss of that receptor provided that the ligand dissociates sufficiently slowly or not at all. To illustrate this point the equilibrium saturation binding curve of ($^{125}I$)-iodohydroxybenzylpindolol was determined in cultured glioma cells. Referring to FIG. 2 the specific binding of ($^{125}I$)-iodohydroxybenzylpindolol ($^{125}I$-HYP), i.e., the difference between total binding and non-specific binding observed in the presence of 1 μM (−)-propranolol, was measured as a function of radioactive ligand concentration in washed control cells (●) and cells treated with 80 nM aminobenzylpropranolol (0) for 40 minutes (37° C.) and washed for 3 hours. For all data points, n=3. The maximum binding capacity was diminished 70% in aminobenzylpropranolol-treated cells, even after prolonged washing, but the equilibrium dissociation constant ($K_D$) for ($^{125}I$)-iodohydroxybenzylpindolol (60 pM) was not different from control runs. This apparent loss of receptors was not accomplished by a change in the affinity of the remaining receptors for ($^{125}I$)-iodohydroxybenzylpindolol.

Figure 3:
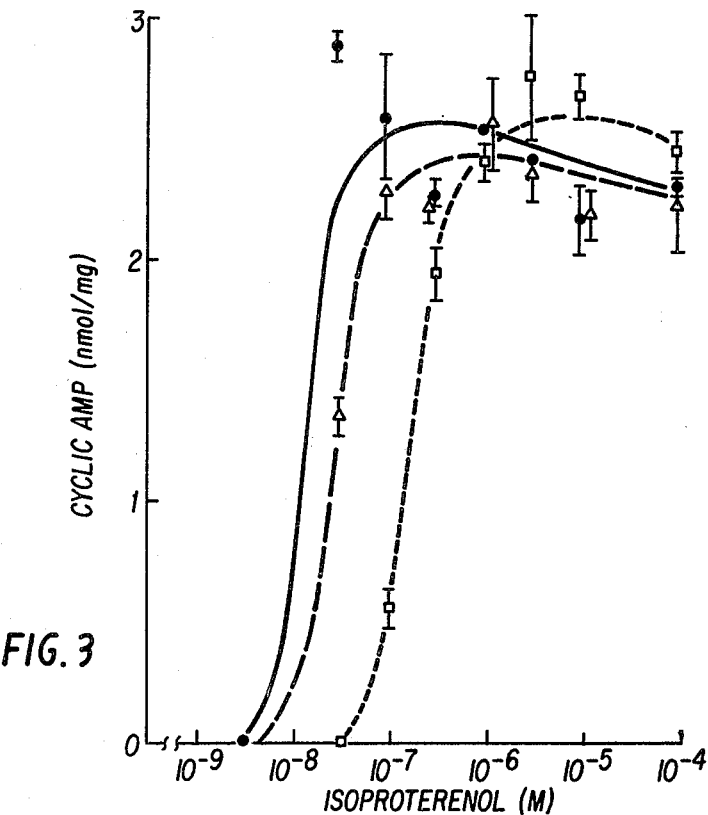
FIG. 3 shows the aminobenzylpropranolol inhibition of increases in intracellular cyclic AMP in isoproterenol-treated glioma cells.

Another aspect of the β-adrenergic blocking activity of aminobenzylpropranolol can be appreciated by reference to FIG. 3 which shows the isoproterenol dose response curves for intracellular cyclic adenosine, 3'5' monophosphate (AMP) accumulation in cultured glioma cells pretreated with aminobenzylpropranolol. In the study glioma cells were treated for 40 minutes with zero (●), 0.1 μM (Δ) or 1 μM (□) aminobenzylpropranolol and then washed with salt solution for 3 hours at 37° C. After washing, the cells were treated for 20 minutes with ((−)-isoproterenol) and extracted with HCl to determine the amount of cyclic AMP. For all data points, n=3.

The curves in FIG. 3 show aminobenzylpropranolol inhibited increases in the intracellular cyclic AMP in isoproterenol-treated glioma cells. This inhibition was observed only at submaximal concentrations of the catecholamine, and isoproterenol dose response curves were shifted to the right. While 0.1 μM and 1 μM aminobenzylpropranolol increased the apparent activation constants for isoproterenol by 0.4 and 1.1 log units respectively, there was no change in the maximal attainable level of intracellular cyclic AMP. A concentration of 1 μM aminobenzylpropranolol was sufficient to eliminate better than 95% of the β-adrenergic receptors (see FIG. 1).

Experiments were also conducted to determine the extent of aminobenzylpropranolol antagonism to isoproterenol-stimulated contractility in isolated atria. For the tests atrial preparations were obtained by excising hearts from 200–250 g male Wistar rats or 300–400 g male Hartley guinea pigs. All of the animals were pretreated with reserpine (5 mg/kg) administered interperitoneally 15–18 hours before the animals were killed by a blow to the back of the neck. Left atria were maintained at 30° C. (pH 7.4) in buffer containing: 118 mM NaCl, 4.75 mM KCl, 1.2 mM $KH_2PO_4$, 1.2 mM $MgSO_4$, 5.5 mM dextrose, 25 mM $NaHCO_3$, and 1 mM $CaCl_2$. The buffer was vigorously bubbled with 95% $O_2$-5% $CO_2$. Atria hooked to platinum-iridium electrodes were stimulated at 1 second intervals with 10 msec monophasic pulses at twice the threshold voltage for contractions. Developed tension was recorded on Beckman oscillographic recorders (Dynographs) and the signals processed by a DEC LSI-11 microcomputer.

The atria prepared above were used in tests which show that aminobenzylpropranolol inhibits isoproterenol-increased tension development in atria isolated from rats and guinea pigs. The inhibition is time and dose dependent. In the actual tests guinea pig and rat atria were pretreated with zero (●), 0.1 μM (■) or 10 μM (Δ) aminobenzylpropranolol (see FIG. 4) and then washed five times with salt solution to remove free inhibitor. (Transfer of the medium which bathes an atrium which had been treated with aminobenzylpropranolol and subsequently washed to an untreated or fresh atrium showed no inhibitory activity in the medium which suggests that the washing step removes essentially all of the free aminobenzylpropranolol). The cumulative dose response curves to (−)-isoproterenol were determined (n=2–3). At the termination of each experiment, maximum tension was determined by exposing atria to 100 μM isobutylmethylxanthine. The treated atria exhibited decreased sensitivity to isoproterenol.

Figure 4:
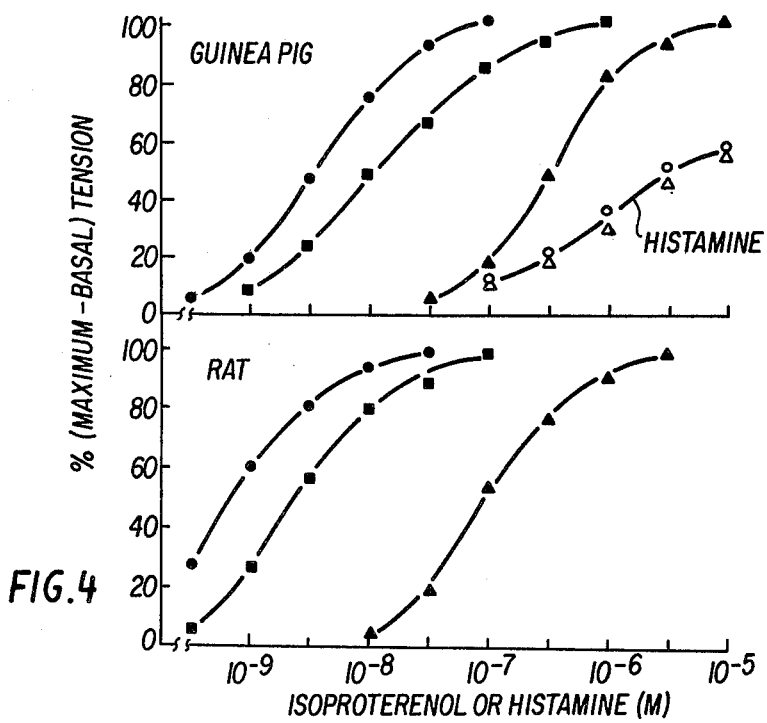
FIG. 4 shows the aminobenzylpropranolol inhibited isoproterenol-increased tension development in atria isolated from rats and guinea pigs.

The degree of inhibition was similar to that observed in glioma cells. As shown in FIG. 4 rat and guinea pig atria pretreated with 0.1 μM and 10 μM aminobenzylpropranolol for 1 hour resulted in 0.5 log and 2 log shifts, respectively, in the cumulative isoproterenol dose response curves. Although the potency of isoproterenol was decreased in aminobenzylpropranolol-treated atria, the efficacy (maximum response) was unchanged. (Efficacy was assessed in two ways: (1) Some atria were pretreated with 0.1 μM isoproterenol—which was maximally effective in the absence of the inhibitor. After washing and treatment with 10 μM aminobenzylpropranolol, the maximal level of tension development remained the same. (2) Efficacy was also assessed by using the phosphodiesterase inhibitor, isobutylmethylxanthine, which is able to elicit a maximal response by itself. Addition of 100 μM isobutylmethylxanthine to atria treated with 10 μM isoproterenol produced a less than 5% increase in developed tension. By both criteria, concentrations of the blocker sufficient to produce a 2 log shift in the potency of isoproterenol did not decrease the efficacy of the catecholamine in atria.) By analogy with the glioma cell experiments, 10 μM aminobenzylpropranolol would be expected to have eliminated by blocking greater than 99% of the tissue β-adrenergic receptors.

FIG. 4 contains the cumulative dose response curves to histamine treated atria (n=2–3). The dose response curve shows that the positive inotropic response of guinea pig atria to histamine was unaltered by aminobenzylpropranolol.

The onset of the inhibitory action of aminobenzylpropranolol was slow. Fold increased in the apparent $K_{Act}$ for isoproterenol were 1.2, 5.2 and 13.5 (1.1 log units) in rat atria pretreated with 1 μM aminobenzylpropranolol for 5, 20 and 50 minutes prior to washing.

Rat atria treated with aminobenzylpropranolol remained blocked even when washed for extended periods of time at 30° C. Rat atria washed 17 hours after treatment with amine (3 μM for 1 hour), showed no detectable decrease in the inhibition of the isoproterenol response compared to parallel washed control tissues: dose response curves remained shifted rightward by 1.5 log units.

If high concentrations of isoproterenol were added to atria pretreated with aminobenzylpropranolol, the catecholamine did not reverse the blockage, even after multiple washes and rechallenges with concentrations of agonist which evoked repeated maximal inotropic responses. In other words, successive isoproterenol dose response curves remained shifted to the right (Multiple exposures of control atria—not pretreated with the inhibitor—to the catecholamine caused a small degree of desensitization (decrease in potency for isoproterenol) with no decrease in efficacy. (For instance, in rat atria the apparent $K_{Act}$ of isoproterenol during the first and second dose response curves was 0.9+, 0.2 nM and 4.7+2.1 nM.) The magnitude of shifts in the curves generated from anagonist-treated tissues was always corrected for this desensitization and are reported relative to identically treated controls).

In an earlier study, it has been shown that C6 rat glioma cells appear to require few of their β-adrenergic receptors in order to respond maximally to adrenergic agonists. This fact was directly inferred from experiments on intact cells which revealed a gross discrepancy between the measured dissociation constant ($K_D$) of pure agonists for ($^{125}I$)—iodohydroxybenzylpindolol binding sites and their apparent activation constant ($K_{Act}$) for cyclic AMP synthesis. In essence, it was shown that the affinity of agonist-binding was much too low to be understood in terms of a simple fixed receptor-cyclase coupling model. In the present invention, the necessity of having a full complement of receptors has been tested directly by measuring biological responses in two dissimilar β-adrenergic systems in which receptor numbers have been diminished by selective chemical means. In both cultured glioma cells and isolated atrial tissues, maximal cyclic AMP or contractile responses were elicited despite a substantial (greater than 95%) decrease in the number of hormone receptors by aminobenzylpropranolol. The molecular mechanism by which persistent blockade by this agent is achieved is unknown, but this is not essential to the argument that physiologic function may be controlled by only a minority of cellular receptors. In both glioma cells and atria, isoproterenol dose response curves were shifted to the right as receptor numbers were artifically decreased. These shifts apparently reflect a decreased interaction of the remaining receptors with adenylate cyclase molecules or other secondary sites which mediate the β-adrenergic response.

The finding that cells which have lost most of their receptors can still manifest full biological responses is not surprising. Takayanagi et al, *Eur. J. Pharmacol,* 38, 595 (1976), attempted to decrease β-adrenergic receptors of guinea pig taenia by photolysis with isoproterenol or 2-(2-hydroxy-3-isopropylaminopropoxy) iodobenzene. When such photolyzed tissues were treated with isoproterenol, potency was decreased, but maximal relaxation could still be elicited. Isoproterenol had decreased potency, but evoked maximal inotropic and cyclic AMP responses in cat papillary muscle, when the receptors had been irreversibly blocked by N-[2-hydroxy-3-(1-naphthoxy)-propyl]-N-bromoacetylethylenediamine.

By contrast, cultured murine S49 lymphoma cells and human VA2 firbroblasts show decreases in their maximal isoproterenol responses when β-adrenergic receptors are persistently blocked. Furthermore, mutant clones of S49 cells, which have been isolated by selecting those cells having diminished cyclic AMP responsiveness, have apparently undergone corresponding losses in β-adrenergic receptors. The resolution of these conflicting observations probably resides in real differences existing between the cell systems examined to date. If one were to pick some cell types over others as being more "physiological," one would tend to choose the isolated muscle preparations rather than the cultured cell lines. It may be more appropriate, however, to consider differences among the systems to be more quantitative than qualitative. It has been hypothesized that adenylate cyclase activation may persist temporarily beyond the time when hormone is bound to the receptor. In order to explain systems such as the heart and glioma cells, a more explicit mechanism would be required where each receptor molecule would have to have access to many, if not all, adenylate cyclase molecules. If after the receptor-cyclase interaction was terminated, the receptors were freed to activate additional enzyme molecules, then full activation despite receptor loss is possible. Such a mode of action has been described as a collision coupling model by Levitzki, *Biochem Pharmacol.,* 27, 2083–2088. The magnitude of the cyclic AMP response (and presumably functions mediated by cyclic AMP) would be some function of the probability that an activating receptor molecule would interact with the cyclase molecule(s). Loss of receptors, whether induced chemically or genetically, would decrease, but not necessarily eliminate, the chance that any given cyclase will be activated. In this way, maximal activation of total cellular cyclase activity could be dependent on many additional and perhaps cell-specific factors such as membrane fluidity, the molecular properties of the receptors themselves, and the lag time of the decay of the enzyme active state.

Regardless of the β-adrenergic system studied the phrase "spare receptors" is misleading. Even in those cases where the full efficacy of β-adrenergic agonists is maintained, all the receptors are probably required for full potency. A corollary to this idea is that since many cells display agonist-induced receptor losses, certain tissues would be expected to undergo desensitization (decrease in agonist potency) as opposed to refractoriness (decrease in agonist efficacy). The heart seems to be an example of a tissue showing a desensitization phenomenon; it makes physiological sense that this critical organ would respond to prolonged catecholamine stimulation with a decrease in sensitivity to the hormones rather than with a loss of contractility.

PREPARATION OF AMINOBENZYLPROPRANOLOL

Aminobenzylpropranolol 1-(p-amino-α, α-dimethylphenethylamino)-3-(1-naphthoxy)-2-propanol is an analog of propranolol and has the features generally ascribed to the most potent β-adrenergic antagonists: a methoxy linkage between the 1 position of the naphthalene moiety and the alkyl side chain, and a secondary-alkyl amine group attached to a methyl or dimethyl-substituted α-carbon.

a. Purification of p-Amino-α,α-dimethylphenethylamine

One gram of commercial p-amino-α,α-dimethylphenethylamine (Aldrich 536658-7) was dissolved in 80 ml of chloroform and applied to a 180 ml column of silica gel (Bio-Sil A, 100–200 mesh) in chloroform. The column was washed with 600 ml of chloroform and then successively eluted with chloroform solutions containing 2% methanol (600 ml), 4% methanol (600 ml), 10% methanol (1600 ml) and 33% methanol (1200 ml). Chromatography was monitored by diluting an aliquot of the column eluate 300 fold in methanol and measuring ultraviolet absorbance at 240 nm ($\epsilon = 8750$). Purified p-amino-α,α-dimethylphenethylamine was obtained between 900 and 1600 ml of 10% methanol and in the first 700 ml of 33% methanol. The pooled solutions were evaporated at 22° C. using a flash-evaporator, and the residue was dissolved in 10 ml of n-butanol. The golden-brown solution represented 62% of the starting material and yielded a single fluorescamine-reactive spot (Rf 0.29) on silica gel thin layer chromatography in chloroform:methanol:ammonium hydroxide (50:50:1, v:v:v). The compound was stored as a 0.38 M solution at −15° C. in the dark.

b. Synthesis of α-Naphthyloxy-1-propane-2,3-oxide

1-Naphthol (Sigma, grade III, recrystallized) (432 mg), 1-[1-$^{14}$C]-naphthol (Amersham, 20.1 mCi/mmol) (5μ Ci in 25 μl of ethanol), sodium hydroxide (130 mg), and epichlorohydrin (Aldrich, E105-5) (230 μl) were combined in a glass tube and heated at 60° C. for 20 hours. The cooled reaction mixture was extracted with 2–3 ml of dichloromethane three times. The pooled extracts were evaporated at 60° C., and the residue was dissolved in n-butanol to make a 0.38 M solution (concentration was determined by reading the ultraviolet absorbance of a methanolic solution assuming $\epsilon = 4700$ at 290 nm). The product, an orange solution, was stored at −16° C. in the dark; it was used for synthetic work without further purification.

c. Synthesis of 1-(p-Amino-α,α-dimethylphenethylamino)-3-(1-naphthoxy)-2-propanol Purified p-amino-α,α-dimethylphenethylamine (380μ moles) was combined with one equivalent of α-naphthoxy-1-propane-2,3-oxide in 2 ml of n-butanol and heated for 48 hours at 65° C. The solvent was removed by evaporation at 65° C. in an open beaker. The residue was dissolved in 10 ml of chloroform and applied to a 4 ml column of silica-gel (Bio-Sil A, 100-200 mesh) in chloroform. the column was washed with 40 ml of chloroform and then with 10 ml aliquots of 1.5% methanol in chloroform. Eight 10 ml fractions were collected, and each was analyzed for product by thin layer chromatography on silica gel developed with chloroform:methanol:ammonium hydroxide (50:50:1, v:v:v). Aminobenzylpropranolol migrates with an Rf of 0.82 while the major amine-containing contaminant (as detected by fluorescamine-staining) migrates at Rf 0.29 (presumably this is unreacted starting amine). Those fractions containing aminobenzylpropranolol (usually fractions 2-5) were pooled and evaporated to dryness at room temperature. The residue was taken up with 10 ml of chloroform, applied to a second silica gel column, and rechromatographed as described above. The fractions containing pure product (single spot by thinlayer chromatography) were pooled, evaporated, dissolved in methanol, and stored at −16° C. in the dark. Overall yield was 25% as determined by recovery of $^{14}C$ radioactivity in the 1 position of the naphthalene residue. Ultraviolet spectra showed a maximum at 290 nm ($\epsilon=4900$).

The product was judged to be pure by a number of criteria. It migrated as a single ninhydrin or fluorescamine-staining spot in the following silica-gel thin layer systems (proportions given by volume): n-propanol: cyclohexane: acetic acid (3:1:1, Rf 0.21); n-butanol:acetic acid: H$_2$O (24:6:10, Rf 0.42); n-butanol: HCl (10:1, Rf 0.60); 0.5 M ammonium formate, pH 8.5:methanol (1:1, Rf 0.62); chloroform:methanol:HCl (66:33:1, Rf 0.63); methanol: HCl (10:1, Rf 0.66); diethylamine:ethyl acetate (1:1, Rf 0.72); 95% ethanol: NH$_4$OH (4:1, Rf 0.80); chloroform: methanol:NH$_4$OH(50:50:1, Rf 0.81); and methanol:1 M sodium acetate, pH 4.8 (3:1, Rf 0.82). By high pressure liquid chromatography, it appeared as a single ultraviolet absorbing peak (Partisil SCX column eluted with 10% methanol, 0.1 M ammonium phosphate, pH 4.3). Chemical ionization mass spectrometry with methane determined a molecular weight of 364.

The primary amine formed by the present synthetic scheme is clearly the aryl amine and not the alkyl amine. It is readily converted to the aryl azide by conventional procedures (Bayley, H. et al, *Methods in Enzymology*, 46, 69-114 (1977)), and the azido derivative shows a shift in absorption maximum to shorter wave lengths with a typical increase in extinction coefficient ($\epsilon_{max}=13,000$ at 275 nm). In addition, mass spectrometry revealed a major ionized fragment of molecular weight 258 which corresponds to the isopropylamine (1-naphthoxy) propanol cleavage product. Such a product could not be obtained from the alkyl amine. Lastly, phenylamino (1-naphthoxy) propanol is devoid of biological activity as described by Crowther, A. F. et al, *J. Med. Chem.*, 11, 1009-1013 (1968).

Having now fully described this invention, it will be apparent to one of ordinary skill in the art that many changes and modifications can be made thereto without departing from the spirit or scope of the invention as set forth herein.

What is claimed as new and desired to be secured by Letters Patent of the United States is:

1. 1-(p-Amino -α,α-dimethylphenethylamino)-3-(1-naphthoxy)-2-propanol and the pharmaceutically acceptable acid addition salts thereof.

2. A method of inducing β-adrenergic receptor blocking activity in a host subject, comprising: administering to said host subject a physiologically effective amount of the compound of claim 1.

3. A therapeutic composition possessing β-adrenergic receptor blocking activity, comprising:
   a physiologically effective amount of the compound of claim 1 with a pharmaceutically acceptable carrier.

* * * * *